United States Patent [19]

Williams et al.

[11] 4,218,513

[45] Aug. 19, 1980

[54] POLYMER COMPOSITE ARTICLES CONTAINING AMINO SUBSTITUTED MERCAPTO ORGANO SILICON COUPLING AGENTS

[75] Inventors: Thomas C. Williams, Ridgefield, Conn.; George E. Totten, West Haverstraw, N.Y.

[73] Assignee: Union Carbide Corporation, New York, N.Y.

[21] Appl. No.: 12,482

[22] Filed: Feb. 15, 1979

Related U.S. Application Data

[62] Division of Ser. No. 810,786, Jun. 28, 1977, Pat. No. 4,156,677.

[51] Int. Cl.$^2$ ............... B32B 17/04; B32B 17/10; C08K 9/06
[52] U.S. Cl. ............... 428/419; 428/420; 428/429; 428/447; 428/450
[58] Field of Search ............... 428/420, 419, 447, 450, 428/429

[56] References Cited

U.S. PATENT DOCUMENTS

| | | | |
|---|---|---|---|
| 3,278,484 | 10/1966 | Tesoro | 260/37 EP |
| 3,297,473 | 1/1967 | Bulbenko | 428/419 |
| 3,328,451 | 6/1967 | Bulbenko | 528/374 X |
| 3,468,751 | 9/1969 | Tesoro | 428/419 |
| 3,768,537 | 10/1973 | Hess et al. | 260/42.44 X |
| 4,005,116 | 1/1977 | Griffiths | 528/24 X |

*Primary Examiner*—Harold Ansher
*Attorney, Agent, or Firm*—Richard J. Gallagher

[57] ABSTRACT

Polymer composites, such as rubber, thermoset and thermoplastic articles, comprising the reaction product of (a) an organic polymer, (b) an inorganic substrate and (c) an amino substituted mercapto organosilicon coupling agent, and articles comprising an inorganic substrate treated with an amino substituted mercapto organosilicon coupling agent.

21 Claims, No Drawings

POLYMER COMPOSITE ARTICLES CONTAINING AMINO SUBSTITUTED MERCAPTO ORGANO SILICON COUPLING AGENTS

This application is a divisional of copending U.S. application Ser. No. 810,786 filed June 28, 1977, now U.S. Pat. No. 4,156,677.

BACKGROUND OF THE INVENTION

This invention relates to novel polymer composite articles of manufacture comprising the reaction product of (a) an organic polymer (b) an inorganic substrate and (c) an amino substituted mercapto organosilicon coupling agent, as well as to articles of manufacture comprising an inorganic substrate treated with an amino substituted mercapto organosilicon coupling agent.

The use of various silicon coupling agents to enhance the adhesion of various inorganic substrates with a broad variety of organic polymers to promote coupling and bonding therewith is well known in the art. Note, for example, U.S. Pat. Nos. 2,832,754; 2,971,864; 3,258,477; 3,661,628; 3,671,562; 3,705,911; 3,706,592 and 3,754,971; and the like. Thus, as is conventionally understood in the art the silicon coupling agent serves as a crosslinker that is chemically or physically bonded to both the inorganic substrate and the organic polymer in the polymer composite.

SUMMARY OF THE INVENTION

Accordingly, it is an object of this invention to provide polymer composite articles of manufacture comprising the reaction product of (a) an organic polymer, (b) an inorganic substrate and (c) a novel amino substituted mercapto organosilicon composition of matter as disclosed in the concurrently filed U.S. Application No. 810,840 now U.S. Pat. No. 4,147,712. It is another object of this invention to provide articles of manufacture comprising an inorganic substrate treated with said novel amino substituted mercapto organosilicon compositions of matter. Other objects and advantages of this invention will become readily apparent from the following description and appended claims.

More specifically then, one embodiment of this invention relates to a polymer composite article of manufacture comprising the reaction product of (a) an organic polymer, (b) an inorganic substrate, and (c) an amino substituted mercapto organosilicon coupling agent selected from the class consisting of (i) amino substituted mercapto organosilane compounds having the formula

wherein R' is a monovalent hydrocarbon radical selected from the class consisting of hydrogen, hydrocarbon radicals and substituted hydrocarbon radicals;
wherein X is a hydrolyzable radical selected from the class consisting of alkoxy, aryloxy, acyloxy, secondary amino and aminooxy radicals;
wherein R is a divalent bridging group selected from the class consisting of hydrocarbon radicals, groups of the formula —R″OR″— and the groups of the formula —R″SR″—, wherein R″ is a divalent hydrocarbon radical;
wherein Q is an oxygen atom or a sulfur atom;
wherein Z is a monovalent organic amino radical the nitrogen atom of which is directly bonded to the carbon atom of the CH$_2$ group of the above formula;
wherein n has a value of 0 or 1 and t has a value of 0 or 1, with the proviso that when n is 0, then t is 0;
wherein a has a value of 1 to 3 and b has a value of 0 to 2, with the proviso that the sum of (a+b) is not greater than 3;
(ii) amino substituted mercapto organosiloxanes consisting essentially of siloxy units having the formula

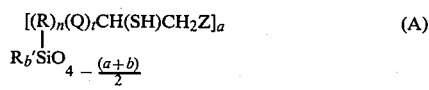

wherein R', R, Q, Z, n, t, a and b are the same as defined above; and (iii) amino substituted mercapto organosiloxane copolymers consisting essentially of at least one siloxy unit represented by formula (A) above and at least one siloxy unit represented by the formula

wherein R' is the same as defined in formula (A) above and wherein c has a value of from 0 to 3 inclusive.

DESCRIPTION OF THE PREFERRED EMBODIMENTS

The polymer composite articles of manufacture of this invention can correspond to any heretofore conventional polymer composite comprising an organic polymer bonded to an inorganic substrate through the use of conventional silicon coupling agents, the difference being that the polymer composite articles of manufacture of this invention employ as the coupling agent, the above referred to amino substituted mercapto organosilicon compositions of matter. Thus, the polymer composite articles of manufacture of this invention include such conventional articles as rubber, thermoplastic and thermosetting resins, paints, varnishes, inks, and the like.

The organic polymer components of the novel composites of this invention as well as methods for their preparation are well known in the art and include a wide variety of polymers. Illustrative examples of such polymers, either singularly or in adjuncture with each other include any of the homopolymers and copolymers of olefinic and diolefinic monomers such as ethylene, propylene, butylenes, methylpentenes, styrene, ring substituted styrenes, alphamethyl styrene, vinyl chloride, vinyl fluoride, vinylidine chloride, acrylonitrile, methacrylonitrile, vinyl alcohol esters, acrylic acid and its esters and amides, methacrylic acid and its esters and amides, allyl phthalate esters, butadiene, isoprene, chloroprene, ethylidene norbornene, 1,5-hexadiene, divinyl benzenes and the like, as well as synthetic condensation polymers commonly classed as alkyd resins, polyesters, nylons, phenolics, epoxides, polysulfones, polysulfonates, polysulfonamides, polysulfides, polyurethanes, polyureas and the like, as well as oligomers and polymers derived from plant and animal sources such as cellulose esters and ethers, carbon-carbon unsaturated fatty acid triglycerides and natural hevea and ficus rubbers and the like.

The more preferred organic polymers employable in this invention are the conventional thermoplastic forming resins, thermoset forming resins, and rubber forming polymers. Illustrative of some of the more preferred thermoplastic forming resins include, e.g. polyethylene, polypropylene, polystyrene, polyvinyl chloride, polyvinyl butyral, nylon, polyacrylonitrile, polycarbonates, polyesters, and the like as well as copolymers and terpolymers thereof. Illustrative of some of the more preferred thermoset forming resins include, e.g. unsaturated polyesters, epoxies, phenolics, melamine, and the like.

The most preferred organic polymers employable in this invention are the conventional vulcanizable unsaturated rubber polymers used to prepare vulcanized rubber compounds. Illustrative of such vulcanizable rubber polymers are natural rubber and synthetic rubber polymers as disclosed, e.g. in The Elastomer Manual (1972 Edition) published by International Institute of Synthetic Rubber Producer, Inc., such as styrene-butadiene rubber polymers, butadiene rubber polymers, ethylene-propylene rubber terpolymers, chloroprene rubber polymers, nitrile rubber polymers, bromo- and chlorobutyl rubber polymers polyisoprene rubber polymers, and the like. Especially preferred are the conventional sulfur vulcanizable rubber polymers such as natural rubber, styrene-butadiene rubber polymers, butadiene rubber polymers, and polyisoprene rubber polymers.

The inorganic substrates employable in this invention are well known in the art and include any conventional inorganic substrate generally employed in bonding to rubber, thermoplastic and thermosetting resins, paints varnishes, inks and the like, and which are substantially reactive toward the amino substituted mercapto organosilicon coupling agents employed in this invention. Illustrative examples of such inorganic substrates include such reinforcing materials, pigments or fillers as siliceous materials such as plate glass, glass fibers, asbestos, sand, clay, talc, silica, e.g. hydrated silica, precipitated silica, fumed silica, silica aerogels, silica xero-gels, metal silicates, e.g. aluminum silicate, calcium silicate, calcium metasilicate, magnesium silicate, feldspar, concrete, ceramic materials and the like; metals such as aluminum, copper, cadmium, chromium, magnesium nickel, silver, tin, titanium, zinc, and the like; the alloys of such metals as brass, bronze, steel, and the like including metals which have been surface treated with phosphates, chromates, and the like; metal oxides such as aluminum oxide, iron oxides, lead oxides, titanium dioxide, zinc oxide and the like. Of course, it is understood that the particular configuration of the inorganic substrate employed is not critical and that the inorganic materials can be in any various form such as sheets, plates, blocks, wires, cloth, fibers, filaments, particles, powders, and the like. The preferred inorganic substrates are the siliceous materials, especially silica and metal silicate fillers or pigments.

The substituted silicon compositions of matter employable in this invention are those amino substituted mercapto organosilanes and organosiloxanes disclosed in said concurrently filed U.S. Application Serial No. 810,840 the entire disclosure of which is encompassed herein by reference thereto.

More specifically such amino substituted mercapto organosilicon compositions of matter include the amino substituted mercapto organosilane compounds of the formula:

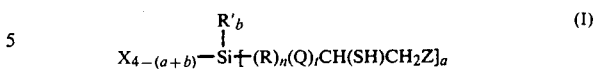

wherein X, R, R', Q, Z, a, b, n, and t are the same as defined above.

Illustrative radicals represented by R' in formula (I) above are hydrogen and monovalent hydrocarbon radicals which can contain from 1 to 20 carbon atoms, and can be unsubstituted or substituted with substituents which are inert under the reaction conditions employed in preparing the silane compounds of this invention. Such hydrocarbon radicals include straight and branched chain alkyl radicals (e.g. methyl, ethyl, n-propyl, isopropyl, n-butyl, isobutyl, t-butyl, n-pentyl, n-hexyl, 2-ethylhexyl, n-decyl, n-dodecyl, n-tetradecyl, n-hexadecyl, n-octadecyl, eicosyl and the like); alkenyl radicals (e.g. vinyl, allyl, 2,4-hexadienyl, 9,12,15-octadecatrienyl, and the like); cycloalkyl radicals (e.g. cyclopentyl, cyclohexyl, and the like); aryl radicals (e.g. phenyl, naphthyl, biphenyl, and the like); cycloalkenyl radicals (e.g. 3-cyclohexenyl and the like); aralkyl radicals (e.g. p-methylphenyl, p-cyclohexylphenyl, alphamethylnaphthyl, and the like); haloaryl radicals (e.g. 4-chlorophenyl 2,4,-dichlorophenyl, chloronaphthyl, and the like); nitroaryl radicals (e.g. 4-nitrophenyl, and the like); cyano-alkyl radicals (e.g. beta-cyanoethyl, gamma-cyanopropyl, and the like). Of course, it is understood that each R' radical can be the same or different in any given silane compound. Preferably R' is hydrogen or a monovalent unsubstituted hydrocarbon radical. More preferably R' is an alkyl radical containing from 1 to 18 carbon atoms and most preferably from 1 to 8 carbon atoms.

Illustrative hydrolyzable radicals represented by X in formula (I) above include alkoxy radicals, (e.g. methoxy, ethoxy, propoxy, isopropoxy, 2-methoxyethoxy, dodecyloxy, betacyanoethoxy, betachloroethoxy, and the like); aryloxy radicals (e.g. phenoxy, 4-chlorophenoxy, and the like); acyloxy radicals (e.g. formyloxy, acetoxy, and the like); secondary amino radicals such as dialkylamino (e.g. dimethylamino, diethylamino and the like) and aminooxy radicals such as dialkylaminooxy (e.g. diethylaminooxy, and the like); Of course, it is understood that each X radical can be the same or different in any given silane compound, although normally it is preferred that each X be the same. Preferably X is an alkoxy radical such as those selected from the group consisting or methoxy, ethoxy and 2-methoxyethyloxy.

Illustrative divalent bridging radicals represented by R in formula (I) above include hydrocarbon radicals, oxygen containing hydrocarbon radicals (i.e. —R'-'OR"—) and sulfur containing hydrocarbon radicals (i.e. —R"SR"—). Normally such radicals contain from 1 to 12 carbon atoms. Illustrative divalent hydrocarbon radicals represented by R include alkylene radicals (e.g. methylene (—CH$_2$—) ethylene, propylene, isopropylene, butylene, neopentylene, pentylene, 2-ethylhexylene, dodecylene, and the like; arylene radicals (e.g. phenylene and the like); arylene containing alkylene radicals (e.g. methylenephenylene —(CH$_2$C$_6$H$_4$—), and the like); The oxygen containing hydrocarbon radicals represented by R are those of the formula —R"OR"—, wherein R" is a divalent hydrocarbon radical, such as alkyleneoxyalkylene radicals (e.g. ethyleneoxymethylene (—C$_2$H$_4$OCH$_2$—), propyleneoxymethylene (—CH$_2$CH$_2$CH$_2$O—CH$_2$—), ethyleneoxyethylene (—C$_2$H$_4$OC$_2$H$_4$—), propyleneoxyethylene (—C$_3$H$_6$OC$_2$H$_4$—), propyleneoxypropylene (—C$_3$H$_6$OC$_3$H$_6$—) and the like); aryleneoxyalkylene radicals (e.g. phenyleneoxymethylene (—C$_6$H$_4$OCH$_2$—), and the like); and the like. The sulfur (or thio) containing hydrocarbon radicals represented by R are those of the formula —R"SR"— wherein R" is a divalent hydrocarbon radical such as alkylenethioalkylene radicals (e.g. ethylenethiomethylene (—C$_2$H$_4$SCH$_2$), propylenethiomethylene (—C$_3$H$_6$SC$_2$H$_4$—) propylenethiopropylene (—C$_3$H$_6$SC$_3$H$_6$—) and the like); arylenethioalkylene radicals (e.g. phenylenethiomethylene (—C$_6$H$_4$SCH$_2$—), and the like); and the like. Preferably R is an alkyleneoxyalkylene radical wherein each divalent alkylene radical contains from 1 to 3 carbon atoms, the most preferred R bridging group being propyleneoxymethylene (—CH$_2$CH$_2$CH$_2$OCH$_2$—).

As pointed out above, when n has a value of 0, then t has a value of 0 and the silicon atom is directly bonded to the carbon atom of the (CH) group in formula (I) above. However, when n has a value of 1, then t can have a value of 0 or 1. The preferred silanes of formula (I) above are those wherein a has a value of 1, b has a value of 0, and n has a value of 1.

The monovalent organic amino radicals represented by Z in above formula (I) include any organic amino radical derived by removing a hydrogen atom from the nitrogen atom of a corresponding organic primary or secondary amine employed in the preparation of the amino sutstituted mercapto organosilane compounds of this invention as explained more fully below. Thus, illustrative monovalent organic amino radicals represented by Z in formula (I) include the corresponding organic amino radicals derived by removing a hydrogen atom from the nitrogen atom of such amines as ethylamine, dimethylamine, diethylamine, di-n-butylamine, sec-butylamine, n-octylamine, 2-hydroxyethylamine bis-(2-hydroxyethyl)amine, 2-methoxyethylamine, 3-hydroxy-propylamine, aniline, ortho and para toluidines, ortho and para aminophenols, p-anisidine, p-dimethylaminoaniline, O- and p- chloro anilines, p-acetamidoaniline, benzylamine, o-mercaptoaniline, m-aminophenyltrimethoxysilane, 2-aminopyridine, 5-amino-2-mercaptobenzothiazole, cyclohexylamine, cyclohexylmethylamine, N-methylaniline, 2-naphtylamine, ethylenediamine, diethylene triamine, p-phenylenediamine, oxydianiline, 2-mercaptoethylamine, allylamine, 3-aminocrotononitrile, piperonylamine, piperazine, piperidine, morpholine, 3-(phenylamino) propyltrimethoxysilane, p-aminodiphenylamine, 3-(n-butylaminopropyl)trimethoxysilane, and the like.

Alternatively then the organic amino radicals represented by Z as discussed above may be those of the formula NZ$^1$Z$^2$ wherein Z$^1$ is an organic radical and Z$^2$ is hydrogen or an organic radical when Z$^1$ and Z$^2$ are taken individually, and when Z$^1$ and Z$^2$ are taken together with the nitrogen atom of the above formula they form a heterocyclic radical.

Accordingly, the more preferred amino substituted mercapto organosilane compounds are those having the formula $$X_3Si—R—CH(SH)CH_2—Z$$

wherein X is a hydrolyzable radical as defined above, especially an alkoxy radical such as methoxy, wherein R is a divalent alkylene or alkyleneoxyalkylene bridging radical as defined above, especially alkyleneoxyalkylene radicals, such as propyleneoxymethylene and wherein Z is an organic amino radical as defined above, especially an amino radical of the formula —NZ$^1$Z$^2$, wherein Z$^1$ and Z$^2$ are taken individually and Z$^1$ is an organic radical selected from class consisting of alkyl, aryl, aralkyl and alkaryl radicals which radicals may be unsubstituted or substituted with substituent radicals which do not adversely affect the preparation of the silane compounds, such as hydroxy, alkoxy, mercapto, amino (e.g. NH$_2$, N(CH$_3$)$_2$, NHC$_6$H$_5$, NHC$_2$H$_4$N(CH$_3$)$_2$, etc.) and hydrolyzable silyl (e.g. —SiOCH$_3$)$_3$ substituted alkyl, aryl, aralkyl, and alkaryl radicals, haloaryl (e.g. 4-chlorophenyl etc.) radicals, and the like, and wherein Z$^2$ is hydrogen or a Z$^1$ radical as defined above, most preferably Z$^1$ is an aralkyl radical such as toluidinyl, especially p-toluidinyl and Z$^2$ is hydrogen.

The amino substituted mercapto organosilanes employed in this invention can be conveniently prepared by reacting the novel episulfide substituted organosilanes disclosed in the concurrently filed U.S. Application No. 810,851, now abandoned, the entire disclosure of which is incorporated herein by reference thereto, with a primary or secondary organic amine as shown by the following equation.

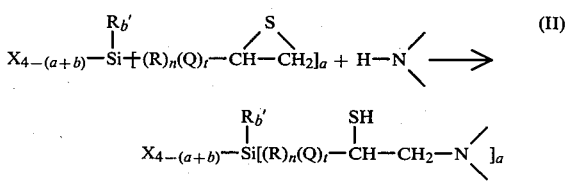

wherein X, R', R, Q, a, b, n and t are the same as defined in formula (I) above and H—N< is a primary or secondary organic amine. More specifically said process can be illustrated as follows:

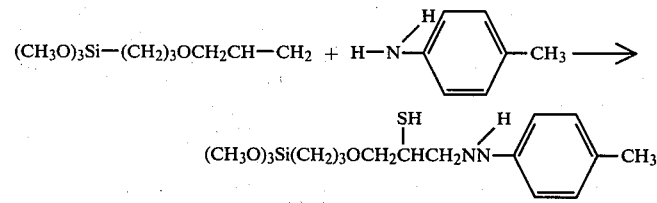

As seen by the above equations the episulfide (or thiiranyl) group on the silane is opened to form the desired mercapto radical (—SH) and provide the bonding to the amino radical derived from the primary or secondary amine reactant, thus resulting in the desired corresponding amino substituted mercapto organosilicon products.

The episulfide substituted organosilanes which can be employed to prepare the amino substituted mercapto organosilanes of this invention can themselves be prepared in any nymber of ways such as described in said concurrently filed U.S. application, Ser. Nos. 810,851 and 810,840.

Preferably the episulfide substituted organosilanes are prepared by reacting a corresponding epoxide containing silane with thiourea as shown by the following equation:

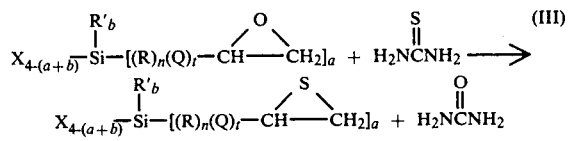

wherein X, R', R, Q, a, b, n and t are the same as defined above. More specifically said process can be illustrated as follows:

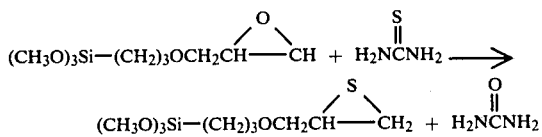

Alternatively, the episulfide substituted organosilanes can also be prepared by reacting a corresponding epoxide containing silane with a metal thiocyanate salt as shown by the following equation:

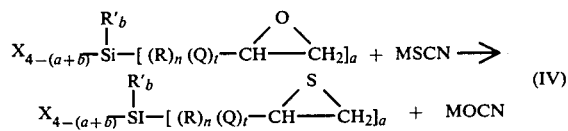

wherein X, R', R, Q, a, b, n and t are the same as defined above and M is a metal such as an alkali metal. More specifically said process may be illustrated as follows:

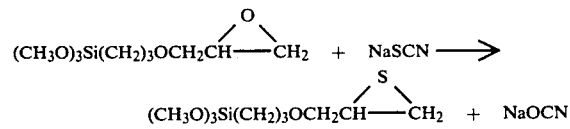

As seen by the above equations the oxygen atom of the epoxide radical of the starting material is replaced by the sulfur atom of the thiourea or metal thiocyanate salt to form the desired episulfide radical thus resulting in the desired corresponding episulfide substituted oranosilane products.

The reaction compounds, i.e. epoxide containing silanes, thiourea or metal thiocyanate salts, and/or methods for their production, which can be used in the above described processes III and IV are well known in the art. Illustrative metal thiocyanate salt starting materials include, e.g. the alkali metal thiocyanate such as NaSCN, KSCN and the like.

The process factors involved in forming the episulfide substituted organosilanes by either of the above two described preferred methods (III) and (IV) are not critical although certain practical choices may be made as described below.

As pointed out above, the two methods of preparation merely involve reacting a corresponding epoxide containing silane with thiourea, Process (III), or a metal thiocyanate salt, Process (IV), and maintaining the reaction until the oxygen atoms of the epoxide starting material has been replaced with the sulfur atom of the thiourea or metal thiocyanate salt to form the desired episulfide substituted organosilane.

No special catalysts are needed for either process. It is advantageous, however to employ a polar solvent. Suitable solvents include aliphatic alcohols, such as methanol, ethanol, n-propanol, t-butanol, and the like. The amount of solvent used is not narrowly critical, the solvent normally being employed in an amount sufficient to dissolve the reactants involved, although lower or higher amounts can be employed if desired. Of course, it is to be understood that the solvent employed should be chosen so as to not adversely react with the hydrolyzable groups on the starting silane or otherwise adversely affect the desired reaction.

In general, both processes (III) and (IV) described above merely involve mixing both reactants and the solvent and maintaining the resultant solubilized mixture at the reaction temperature until the reaction has been completed. Any convenient order of mixing can be employed. In both processes stoichiometric amounts of reactants can be used, while it may sometimes be advantageous to use an excess of urea or metal thiocyanate in order to increase the yield or the reaction rate. Both processes are generally conducted at atmospheric pressure, although subatmospheric or superatmospheric pressure may be used if desired. It is also preferred that said processes (III) and (IV) be initially conducted in a substantially anhydrous environment due to the reactivity of the reactants and products towards water, thus both processes are normally carried out under a dry nitrogen atmosphere.

The reaction temperature for both processes (III) and (IV) are not narrowly critical and can range from about room temperature up to and including the reflux temperature of the reaction mixture as may be convenient for the operator, the most preferred reaction temperature for any specific reaction being obviously easily determinable by routine experimentation. Both processes (III) and (IV) are generally completed within from about one to about four hours but may be completed faster or take longer depending on such obvious factors as the amounts and types of reactants involved, and the solvent and reaction temperature employed. Completion of said reactions is generally easily determinable e.g. by the cessation of any further formation of solid urea or cyanate salt by-product. The solvent employed and the by-products of said preferred processes (III) and (IV) can be easily removed, and the desired normally liquid episulfide substituted silane products recovered by any suitable conventional method. For example, the solvent can be removed by distillation and the solid by-products by filtration, centrifuging and the like. The episulfide substituted organosilanes can be advantageously employed in their crude product form or, if desired, undergo conventional treatment procedures in order to obtain a purer product prior to use.

Any organic primary or secondary amine which will function as described above in process (II) may be employed to prepare the amino substituted mercapto organosilanes employed in this invention and such amine compounds and/or methods for their preparation are well known in the art. Illustrative examples of such primary and secondary amine reactants include such amines as methylamine, ethylamine, dimethylamine, diethylamine, di-n-butylamine, sec-butylamine, n-octylamine, 2-hydroxyethylamine, bis-(2-hydroxyethyl)amine, 2-methoxyethylamine, 3-hydroxypropylamine, aniline, ortho and para toluidines, ortho and para aminophenols, p-anisidine, p-dimethylaminoaniline, O- and p-chloroanilines, p-acetamidoaniline, benzylamine, o-mercaptoaniline, m-aminophenyltrimethoxysilane, 2-aminopyridine, 5-amino-2-mercaptobenzothiazole, cyclohexylamine, cyclohexylmethylamine, N-methylaniline, 2-naphthylamine, ethylenediamine, diethylene triamine, p-phenylenediamine, oxydianiline, 2-mercaptoethylamine, allylamine, 3-aminocrotononitrile, piperonylamine, piperazine, piperidine, morpholine, 3-(phenylamino)propyltrimethoxysilane, p-aminodiphenylamine, 3-(n-butylamino)propyltrimethoxysilane, and the like.

The process factors involved in forming the amino substituted mercapto organosilanes used in this invention by the above described process (II) are not critical although certain practical choices may be made as described below.

As pointed out above, process (II) merely involves reacting a corresponding episulfide substituted organosilane with an organic primary or secondary amine and maintaining the reaction until the episulfide group has been opened to form the desired amino substituted mercapto organosilane. No special catalysts are needed for the process. It is advantageous, however, to carry out the process in the presence of a solvent such as hydrocarbons, ethers, esters, alcohols and mixtures thereof. The amount of solvent used is not narrowly critical, the solvent normally being employed in an amount sufficient to dissolve the reactants involved, although lower or higher amounts can be employed if desired. Of course, it is to be understood that the solvent employed should be chosen so as to not adversely react with the hydrolyzable groups on the starting silane or otherwise adversely affect the desired reaction.

In general, process (II) merely involves mixing both reactants and the solvent and maintaining the resultant solubilized mixture at the reaction temperature until the reaction has been completed. Preferably the amount of organic amine employed is at least stoichiometrically equivalent to the number of episulfide groups of the silane to be reacted or moderately in excess of such amounts, although higher or lower amounts of the organic amine may be employed if desired. The process is generally conducted at atmospheric pressure, although subatmospheric or superatmospheric pressures may be used if desired. It is also preferred that said process be initially conducted in a substantially anhydrous environment due to the reactivity of the reactants and products towards water, thus the process is normally carried out under a dry nitrogen atmosphere.

The reaction temperature in above described process (II) is not narrowly critical and can range from about room temperature up to and including the reflux temperature of the reaction mixture as may be convenient for the operator, the most preferred reaction temperature for any specific reaction being obviously easily determinable by routine experimentation. The process is generally completed within from about one to about four hours, but may be completed faster or take longer depending on such obvious factors as the amounts and types of reactants involved, and the solvent and reaction temperature employed. Completion of the reaction is easily determinable e.g. by infrared analysis on a sample of the reaction product for the presence of the mercapto group or by titration of such a sample for the presence of said mercapto group. The solvent employed in the process can be easily removed and the desired amino substituted mercapto organosilane products recovered by any suitable conventional method. For example, the solvent can be removed by stripping at reduced pressures. The amino substituted mercapto organosilanes can be advantageously employed in their crude product form or, if desired, undergo conventional treatment procedures in order to obtain a purer product prior to use.

Illustrative amino substituted mercapto organosilanes that may be derived from their corresponding episulfide substituted organosilane materials and organic primary and secondary amines include

(CH$_3$O)$_3$Si—CH(SH)CH$_2$N(CH$_3$)$_2$

(CH$_3$O)$_3$SiCH$_2$CH(SH)CH$_2$N(CH$_2$)$_2$OCH$_2$CH$_2$

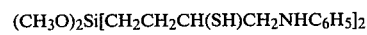
(CH$_3$O)$_2$Si[CH$_2$CH$_2$CH(SH)CH$_2$NHC$_6$H$_5$]$_2$

H
|
(CH$_3$O)$_2$Si(CH$_2$)$_3$CH(SH)CH$_2$NHCH$_2$C$_6$H$_5$

(C$_2$H$_5$O)$_3$Si(CH$_2$)$_3$CH(SH)CH$_2$NHC$_2$H$_5$

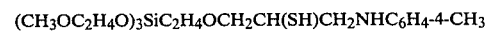
(CH$_3$OC$_2$H$_4$O)$_3$SiC$_2$H$_4$OCH$_2$CH(SH)CH$_2$NHC$_6$H$_4$-4-CH$_3$

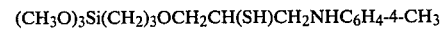
(CH$_3$O)$_3$Si(CH$_2$)$_3$OCH$_2$CH(SH)CH$_2$NHC$_6$H$_4$-4-CH$_3$

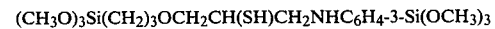
(CH$_3$O)$_3$Si(CH$_2$)$_3$OCH$_2$CH(SH)CH$_2$NHC$_6$H$_4$-3-Si(OCH$_3$)$_3$

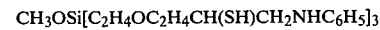
CH$_3$OSi[C$_2$H$_4$OC$_2$H$_4$CH(SH)CH$_2$NHC$_6$H$_5$]$_3$

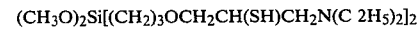
(CH$_3$O)$_2$Si[(CH$_2$)$_3$OCH$_2$CH(SH)CH$_2$N(C$_2$H$_5$)$_2$]$_2$

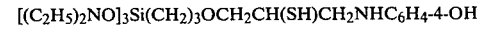
[(C$_2$H$_5$)$_2$NO]$_3$Si(CH$_2$)$_3$OCH$_2$CH(SH)CH$_2$NHC$_6$H$_4$-4-OH -continued (CH₃O)₂—Si(CH₂)₃OCH₂CH(SH)CH₂NH(C₆H₄) (CH₂)₃Si(OCH₃)₂ with CH₃ on Si (C₆H₅O)₃Si(CH₂)₃OCH₂CH(SH)CH₂N(C₂H₅)₂

(CH₃O)₂Si(CH₂)₃CH(SH)CH₂NHC₆H₄-4-CH₃ with CH₃ on Si (CH₃OC₂H₄O)₃Si(CH₂)₃OCH₂CH(SH)CH₂NHC₆H₅

(CH₃$\overset{O}{\overset{\|}{C}}$O)₃Si(CH₂)₃OCH₂CH(SH)CH₂NHC₆H₄-4-OCH₃

(CH₃O)₃Si(CH₂)₃OC₂H₄CH(SH)CH₂NHC₆H₄-2-SH (C₂H₅O)₃Si(CH₂)₃CH(SH)CH₂NHC₆H₄-4-CH₃

[(CH₃)₂N]₃SiC₆H₄OCH₂CH(SH)CH₂NHC₆H₄-4-CH₃

(CH₃O)₃Si(CH₂)₃OC₂H₄OCH(SH)CH₂NH(CH₂)₃Si(OC₂H₅)₃

(CH₃OC₂H₄O)₃SiC₂H₄SCH₂CH(SH)CH₃O)$_{NHC_6H_4\text{-}4\text{-}Cl}$ (CH₃)₃Si(CH₂)₃SCH₂CH(SH)CH₂NHC₆H₅

(CH₃O)₃Si(CH₂)₃SC₂H₄SCH(SH)CH₂N(C₂H₅)₂ and the like.

Alternatively the silicon coupling agent compositions of matter employable in this invention include amino substituted mercapto organosiloxanes. Illustrative of such amino substituted mercapto organosiloxanes are those consisting essentially of siloxy units having the formula $$[(R)_n(Q)_t CH(SH)CH_2 Z]_a \atop R_b'SiO_{4-\frac{(a+b)}{2}} \quad (A)$$

wherein R', R, Q, Z, n, t, a and b are the same as defined above; as well as amino substituted mercapto organosiloxane copolymers consisting essentially of at least one siloxy unit represented by formula (A) above and at least one siloxy unit represented by the formula $$R_c'SiO_{\frac{4-c}{2}} \quad (B)$$

wherein R' is the same as defined in formula (A) above and
wherein c has a value of from 0 to 3 inclusive.

For example, the amino substituted mercapto organosilanes can be hydrolyzed and condensed in the conventional manner, either alone or together with other hydrolyzable silanes to produce siloxanes consisting essentially of the siloxy units of formula (A) above or copolymer type siloxanes consisting essentially of siloxy units of formula (A) above and formula (B) above. When the amino substituted mercapto organosilanes are cohydrolyzed and condensed with other conventional hydrolyzable silanes, the siloxanes produced are copolymers consisting essentially of siloxy units of formula (A) above and formula (B) above. Illustrative conventional hydrolyzable silanes are those of the formula $R_c'$—Si—$X_{4-c}$ wherein R' and c are the same as defined above and X is a hydrolyzable group such as an alkoxy radical, e.g. methoxy.

Thus, in general the amino substituted mercapto organosiloxanes must contain at least one siloxy unit such as

[ZCH₂(SH)CH(Q)$_t$(R)$_n$]Si(R')O,
[ZCH₂(SH)CH(Q)$_t$(R)$_n$]Si(R')₂O$_{0.5}$,
[ZCH₂(SH)CH(Q)$_t$(R)$_n$]SiO$_{1.5}$,
[ZCH₂(SH)CH(Q)$_t$(R)$_n$]₂SiO,
[ZCH₂(SH)CH(Q)$_t$(R)$_n$]₃SiO$_{0.5}$, or
[ZCH₂(SH)CH(Q)$_t$(R)$_n$]₂Si(R')O$_{0.5}$ and may contain one or more siloxy units, such as R'₃SiO$_{0.5}$, R'₂SiO, R'SiO$_{1.5}$, or SiO₂, wherein Z, Q, R, R', t and n are the same as defined above. Of course, it is understood that the siloxanes can also contain a minor amount of hydrolyzable groups if complete hydrolysis is not obtained.

The hydrolysis and condensation of the amino substituted mercapto organosilanes is not critical and can be carried out in any conventional manner, and such procedures are well known in the art. Alternatively, the amino substituted mercapto organosiloxanes can also be prepared by reacting a corresponding episulfide containing organosiloxane with an organic primary or secondary amine in the same manner as described above for producing the amino substituted mercapto organosilanes. However, it is to be understood that when such an alternative method is employed that the siloxanes can also contain hydrolyzable end blocked siloxy units if the starting materials contain same and in those instances wherein less than an equivalent amount of organic amine reactant is employed, the siloxanes can also contain siloxy units having unreacted episulfide groups.

Elemental analysis, C¹³ magnetic nuclear resonance spectroscopy and proton nuclear magnetic resonance spectroscopy confirmed that the amino substituted mercapto compositions of matter used in this invention consist essentially of compositions having the general formula employed herein by showing, e.g. as seen in formula (I) and process (II) above, that the mercapto group (—SH) is essentially bonded directly to the (CH) group of the opened episulfide moiety of the starting silane material, while the amino radical is essentially bonded directly to the (CH₂) group of said opened episulfide moiety. It is to be understood of course that the amino substituted mercapto organosilicon compositions employed in this invention can contain minor amounts (normally not more than 10%) of mercapto groups that are bonded directly to the (CH$_2$) group of said opened episulfide moiety and like amounts of the amino radical bonded directly to the (CH) group of said opened episulfide moiety, since such bonds have also been indicated by said elemental analysis and nuclear magnetic resonance spectroscopy.

The function of a silicon coupling agent to provide a strong chemical bridge between the inorganic substrate and the organic polymer employed is well known in the art. It is of course understood that for effective coupling action in a particular polymer substrate composite, it is necessary to select the appropriate coupling agent, i.e. one which is suitably reactive towards both the polymer component and the substrate component for each particular polymer-substrate composite considered. Thus, while there may be more than one appropriate coupling agent for a particular polymer substrate composite, a given coupling agent may not be appropriate for all polymer composites. However, the selection of the most preferred coupling agent for any particular polymer composite is well within routine experimentation.

The particular manner of compounding the polymer composite articles of manufacture of this invention as well as the various amounts of ingredients employed are not critical and merely depend on the particular finished polymer composite desired along with the ultimate end use for which it is to be employed and such steps as compounding, heating, crosslinking or vulcanizing, and the like, may be conducted in any conventional manner heretofore employed in preparing conventional polymer composites such as thermoplastic resin composites, composites, thermoset resin composites, vulcanized rubber composites, and the like.

For example, in the case of conventional polymer-filler type composites such as vulcanized rubber articles the amino substituted mercapto organosilicon coupling agents and/or solubilized solutions thereof can be added to the vulcanizable rubber polymer batch together with the substrate filler and various other additives during mill or banbury mixing. Alternatively the substrate fillers or vulcanizable rubber polymers can be treated (coated) with the amino substituted mercapto organosilicon coupling agents and/or solubilized solutions thereof prior to incorporation into the rubber polymer or filler master batch. Generally it is preferred to employ the amino substituted mercapto organosilicon coupling agents neat, mix them with the substrate filler, preferably a silica or metal silicate filler, and add the mixture to the polymer batch prior to the incorporation of the other conventional additives normally employed in such polymer filled composites. Moreover, if desired, the episulfide substituted mercapto organosilicon coupling agents can be taken up (adsorbed) on any suitable conventional microporous carrier, e.g. Microcel E, a calcium silicate, prior to use to form a dry free flowing powder concentrate. Such microporous carriers, in the amounts normally used, do not affect the properties of the composite product articles and the free flowing powder concentrate provides convenience in handling and metering of the coupling agent. As pointed out above, the particular procedures involved and amount ratios of the components employed are all within the knowledge of one skilled in the art and are left to the choice of the operator. More specifically, however, the preferred polymer composite articles of this invention are vulcanized rubber articles. Thus, in general, the amount of amino substituted mercapto organosilicon coupling agent employed in the vulcanized rubber composites of this invention will normally range from about 0.1 to about 20 parts by weight (preferably from about 0.2 to about 10 parts by weight) per 100 parts by weight of inorganic substrate filler employed although higher or lower amounts may be employed if desired. Of course, the amount of inorganic substrate filler employed merely depends on the desired rubber product end use and may range from about 5 up to as high as 300 parts by weight or higher per 100 parts by weight of vulcanized rubber polymer employed. The vulcanizable rubber compound is normally vulcanized in the presence of conventional sulfur or peroxide curatives that are well known in the art. For example, a conventional sulfur curative may include per 100 parts by weight of vulcanized rubber polymer from about 0.5 to 4 parts by weight of sulfur, about 2 to 5 parts by weight of zinc oxide, and about 0.2 to 3 parts by weight of accelerators (e.g. diphenylguanidine); while a conventional peroxide curative generally may include per 100 parts by weight of vulcanizable rubber polymer from about 1 to about 8 parts by weight of an organic peroxide e.g. dicumyl peroxide, $\alpha,\alpha'$-bis(t-butyl peroxy) diisopropylbenzene, and the like. The vulcanization procedure of a rubber polymer is well known in the art and in general may be conducted at temperatures ranging from 260° F. to about 360° F. although lower or higher temperatures may be employed if desired. Of course, it is obvious that if desired the vulcanized rubber composites of this invention may contain any of the conventionally additional ingredients such as extenders, carbon blacks, processing oils, plasticizers, antioxidants, lubricants, accelerators, retardants, coloring pigments and dyestuffs and the like, normally employed in conventional vulcanized rubber composites and such is well within the knowledge of one skilled in the art.

In the case of conventional rubber, thermoplastic or thermoset polymer laminate type composites wherein e.g. the inorganic substrate is glass fibers, it is generally preferred to pretreat (coat) the inorganic substrate with the amino substituted mercapto organo-silicon coupling agent prior to bonding with the organic polymer employed although the coupling agent and organic polymer can be deposited together on the substrate and then bonded or the polymer first treated with the coupling agent and then coated onto the substrate and bonded, if desired. The amino substituted mercaptoorganosilicon coupling agent may be employed neat, although it is generally preferred to employ a solubilized solution of the coupling agent by employing an appropriate solvent such as those discussed above, and more preferably to employ an aqueous composition of the amino substituted mercapto organosilicon coupling agent, especially the silane coupling agents. The production of such polymer laminate type composites is well known in the art. The various amounts of compounds employed of course merely depend upon the amino substituted mercapto organosilicon coupling agent employed, the surface area to be covered, the organic polymer to be bonded to the substrate and the like. Moreover, the method of coating the substrate is not critical and the coupling agent can be sprayed, brushed, poured, or rolled on to the surface of the substrate and the like, or alternatively the substrate can be dipped into a solvent solution or aqueous composition of the coupling agent. Likewise the temperature at which the bonding reaction is carried out can be varied over a wide range depending upon the specific compounds employed. In general, heat temperatures will generally be in the range of about 100° C. to about 350° C. or higher, although if desired the bonding between the substrate, coupling agent and organic polymer may also be carried out by the use of ultra-violet radiation, X-rays and the like. Of course, it is obvious that such polymer laminate type composites if desired may contain any of the conventional additional ingredients normally employed in conventional polymerlaminate articles such as catalysts, antioxidants, pigments, and the like.

Accordingly, another aspect of this invention is directed to an inorganic substrate as defined above treated with an amino substituted mercapto organosilicon coupling agent as defined above. When employed aqueous compositions of the coupling agent generally comprise from about 0.1 to about 20 parts by weight of the amino substituted organosilicon coupling agent and from about 99.9 to about 80 parts by weight of water. Such aqueous compositions may be in the form of solutions, dispersions or emulsions and may be especially suitable for use as sizing and finishing agents in the glass fiber industry. If desired the amino substituted mercapto organosilicon coupling agent can be employed in the form of a water-soluble solvent solubilized solution. Generally, it is preferred to employ aqueous compositions of an amino substituted mercapto organosilane coupling agent. Of course, it is to be understood that since the amino substituted mercapto organosilicon coupling agents contain hydrolyzable groups (e.g. alkoxy radicals) the aqueous compositions of such include and encompass the hydrolyzates, partial hydrolyzates, condensates and partial condensates of said silicon coupling agents. The treatment of coating of the inorganic substrate with said aqueous compositions is conventional as discussed above.

Thus, it will be readily apparent to those skilled in the art that the amino substituted mercapto organosilicon coupling agents employed in this invention lend themselves to any conventional process where organic polymers are to be bonded to inorganic substrates and thus to the formation of a wide range of polymer composite articles of manufacture such as filled vulcanized rubber products, filled thermoset and thermoplastic products, organic polymer-substrate (e.g. glass fibers) laminate products, and the like, heretofore prepared with conventional silane coupling agents.

Evidence of action by a coupling agent is manifested through changes in composite properties away from the values displayed in the absence of the agent and the properties which may be favorably altered are many and varied. In elastomeric and resinous composites the improved effects attributable to the instant invention are often seen in terms of its increased resistance to deforming forces and abrasion resistance and in decreased hysteresis losses in flexure. For example, the reactivity and/or bonding between the organic polymer, inorganic substrate and amino substituted mercapto organosilicon coupling agent of this invention is demonstrated by improved physical properties in the finished polymer composite product, such as tensile modulus, and the like as compared to the physical properties of the same finished composite product prepared without the use of the amino substituted mercapto organosilicon coupling agent. Likewise while the amino substituted mercapto organosilicon "coating" per se on the pretreated inorganic substrate articles of this invention is not measurable, its presence is also confirmed by such improved physical properties in the finished polymer composite prepared with such pretreated substrates as compared to the same finished product prepared with an untreated substrate and without the use of any amino substituted mercapto organosilicon coupling agent.

The following examples are illustrative of the present invention and are not to be regarded as limitative. It is to be understood that all parts, percentages and proportions referred to herein and in the claims are by weight unless otherwise indicated. Tensile modulus is defined as tensile stress in pounds per square inch of original cross-sectional area necessary to produce a given extension in a composite specimen, usually 300% of the unstressed length.

EXAMPLE 1

Into a 1-liter, 3-neck flask equipped with a magnetic stirrer, thermometer, and a reflux condenser having a nitrogen by-pass for carrying out the reaction under a nitrogen atmosphere were charged about 269.6 grams of distilled glycidoxypropyltrimethoxysilane, about 86.9 grams of thiourea and about 312.2 grams of methanol. The stirred solubilized reaction mixture was boiled at reflux (about 65° C.) for one hour, then cooled and the methanol solvent stripped out under reduced pressure. The reaction product mixture was then dissolved in diethyl ether and then washed with water to remove the precipitated urea by-product and any unreacted thiourea. The ether solution was then dried with anhydrous magnesium sulfate, filtered, and the ether stripped off under reduced pressure to yield about 234.4 grams of the desired fluid 1,2-epithio-4-oxa-7-trimethoxysilyl heptane crude product which has the formula

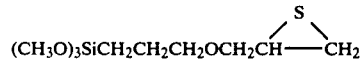

The structure of said crude product was confirmed by infrared absorption spectroscopy, proton magnetic resonance spectroscopy and $C^{13}$ magnetic resonance spectroscopy analysis, as well as by chemical analysis for methoxy and elemental silicon content.

About 40 grams of said crude product were then distilled through a 1-foot Vigreaux column at about 0.18 mm Hg to yield about 35.6 grams of yellowwhite viscous 1,2-epithio-4-oxa-7-trimethoxysilyl heptane oil having boiling points of about 95° C. at 0.07 mm Hg and about 108° C. at 0.18 mm Hg. and a refractive index of $n_D^{20} = 1.460$. The structure for said distilled 1,2-epithio-4-oxa-7-trimethoxysilyl heptane product was confirmed by $C^{13}$ nuclear magnetic resonance spectroscopy, laser Raman spectroscopy and vapor phase chromatography.

A further 100 grams of said crude product was distilled in a like manner to give about 90.1 grams of 1,2-epithio-4-oxa-7-trimethoxysilyl heptane having boiling points of about 107° C. at 0.20 mm Hg. and about 110° C. at 0.25 mm Hg. and exhibited a purity of about 94.1% by vapor phase chromatography analysis.

EXAMPLE 2

Preparation of 1-(trimethoxysilyl)-4-oxa-6-mercapto-8-aza-11-(triethoxysilyl)undecane.

In a 250 cc flask equipped with thermometer, magnetic stirrer, condenser dropping funnel, heater and maintained under $N_2$ atmosphere were placed 11.1 parts by weight of 3-amino-propyltriethoxysilane plus 23.7 parts by weight of isopropyl ether. The stirred mixture was boiled at reflux and 12.6 parts by weight of a crude 1,2-epithio-4-oxa-7-trimethoxysilyl heptane product, prepared as described in Example 1 above was added dropwise. After boiling at reflux for two hours, the mixture was cooled and the ether solvent stripped off under reduced pressure (100° C., 0.6 mm Hg.). Analysis by $C^{13}$ and proton nuclear magnetic resonance spectroscopy and by chemical titrations for mercapto and amine content of the crude product confirmed that a mercapto and amino substituted silane having the formula $(CH_3O)_3Si(CH_2)_3OCH_2CH(SH)CH_2NH(CH_2)_3Si(OC_2H_5)_3$ was produced in a 74% yield (based on titration for the mercapto group).

Analysis of the silane product of an earlier run of this same example indicated the production of 1-(trimethoxysilyl)-4-oxa-6-mercaptomethyl-7-aza-10-(triethoxysilyl)decane, however, such is not considered to be an accurate experiment in view of its lack of duplication by the later run given herein above and in view of the analysis of the products of the examples given herein below.

EXAMPLE 3

Preparation of 1-dimethylamino-2-mercapto-4-oxa-7-(trimethoxysilyl-heptane

In a 500 cc flask equipped with thermometer, condenser, magnetic stirrer, heater, $N_2$ atmosphere and dropping funnel were placed 50.0 parts by weight of hexane plus 7.0 parts by weight of dimethylamine. While gently warming to about 46° C., 25.2 parts by weight of a crude 1,2-epithio-4-oxa-7-trimethoxysilyl heptane product, prepared as described in Example 1 above, was added dropwise. The mixture was boiled at reflux (57° C.) for three hours, cooled and the solvent stripped under reduced pressure. A slight turbidity in the mixture, apparently due to polymer formation was removed by filtration. Analysis by $C^{13}$ and proton nuclear magnetic resonance spectroscopy and by chemical titrations for mercapto and amino content of the product confirmed that a mercapto and amino substituted silane having the formula $(CH_3O)_3Si(CH_2)_3OCH_2CH(SH)CH_2N(CH_3)_2$ was produced in an 80% yield (based on titration for the mercapto group).

EXAMPLES 4 to 23

A variety of mercapto and amino silane compounds were produced according to the general procedure of Example 3 by reacting either a crude 1,2-epithio-4-oxa-7-trimethoxysilyl heptane product prepared as described in Example 1 above (referred to as Silane A in Table I below) or a distilled 1,2-epithio-4-oxa-7-trimethoxysilyl heptane product having a boiling point of about 107° C. at 0.20 mm Hg. prepared as described in Example 1 above (referred to as Silane B in Table I below) with a variety of organoamino compounds as shown in TABLE I below. Analysis by $C^{13}$ and proton nuclear magnetic resonance spectroscopy confirmed the silane product structures for each example, while the given percentage yield of product is based on titration for the mercapto group.

TABLE I

| Ex. No. | 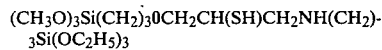 R*—CH—CH₂ (Parts by Wt.) | Organoamino Compound (Parts by Wt.) | Solvent (Parts by Wt.) | °C./Hours | Mercapto, Amino Substituted Silane Product | % Yield |
|---|---|---|---|---|---|---|
| 4 | Silane A (17.6) | Piperidine (11.9) | Hexane (29.5) | R¹/3 | R*CH(SH)CH₂N(CH₂)₄CH₂ | 85 |
| 5 | Silane A (17.6) | Morpholine (12.2) | Hexane (29.8) | R/3 | R*CH(SH)CH₂N(CH₂)₂OCH₂CH₂ | 95 |
| 6 | Silane A (12.6) | Aniline² (13.9) | Methanol (26.5) | R/3 | R*CH(SH)CH₂NHC₆H₅ | 90 |
| 7 | Silane A (12.6) | p-Toluidine² (16.1) | Methanol (28.7) | R/3 | R*CH(SH)CH₂NHC₆H₄-4-CH₃ | 75 |
| 8 | Silane A (12.6) | p-Aminophenol² (16.4) | Methanol (29.0) | R/3 | R*CH(SH)CH₂NHC₆H₄-4-OH | <50 |
| 9 | Silane B (12.6) | p-Anisidine (12.3) | Methanol (24.9) | R/3 | R*CH(SH)CH₂NHC₆H₄-4-OCH₃ | 93 |
| 10 | Silane B (12.6) | p-Dimethylamino-aniline (13.6) | Methanol (26.2) | R/3 | R*CH(SH)CH₂NHC₆H₄-4-N(CH₃)₂ | 86 |
| 11 | Silane B (12.6) | m-aminophenyl-trimethoxysilane (21.3) | Methanol (33.9) | R/3 | R*CH(SH)CH₂NHC₆H₄-3-Si(OCH₃)₃ | 90 |
| 12 | Silane B (12.6) | p-Chloroaniline (12.8) | Methanol (25.4) | R/3 | R*CH(SH)CH₂NHC₆H₄-4-Cl | 72 |
| 13 | Silane (A) (14.8) | 2-Aminopyridine (9.4) | Methanol (23.0) | R/3 | R*CH(SH)CH₂NH—(pyridyl) | <50 |
| 14 | Silane A (14.8) | p-Acetamido-aniline (15.0) | Methanol (30.0) | R/6 | R*CH(SH)CH₂NHC₆H₄-4-NHC(O)—CH₃ | 75 |
| 15 | Silane A (14.8) | 5-Amino-2-mercaptobenzo-thiazole (18.2) | Methanol (30.8) | R/6 | R*CH(SH)CH₂NH—(benzothiazol-C—SH) | <50 |
| 16 | Silane A (29.6) | Benzylamine (25.7) | Hexane (55.3) | R/3 | R*CH(SH)CH₂NHCH₂C₆H₅ | 79 |
| 17 | Silane A | O-Chloroaniline | Isopro- | R/6 | R*CH(SH)CH₂NHC₆H₄-2-Cl | 83 |

TABLE I-continued

| Ex. No. | $R^*-\overset{S}{\underset{\diagup\diagdown}{CH}}-CH_2$ (Parts by Wt.) | Organoamino Compound (Parts by Wt.) | Solvent (Parts by Wt.) | °C./Hours | Mercapto, Amino Substituted Silane Product | % Yield |
|---|---|---|---|---|---|---|
|  | (14.6) | (14.8) | panol (29.4) |  |  |  |
| 18 | Silane A (14.8) | p-Aminodiphenyl-amine (9.2) | Methanol (33.2) | R/3 | R*CH(SH)CH$_2$NHC$_6$H$_4$NHC$_6$H$_5$ | 94 |
| 19 | Silane A (10.9) | o-Aminophenol (10.9) | Methanol (25.0) | R/3 | R*CH(SH)CH$_2$NHC$_6$H$_4$-2-OH | 92 |
| 20 | Silane A (15.1) | o-Mercapto-aniline (12.5) | Methanol (27.6) | R/4 | R*CH(SH)CH$_2$NHC$_6$H$_4$-2-SH | 98 |
| 21 | Silane A (15.1) | 2-(Phenylamino)-propyltrimethoxy-silane (28.5) | Methanol (50.0) | R/3 | R*CH(SH)CH$_2$N(C$_6$H$_5$)(CH$_2$)$_3$Si-(OCH$_3$)$_3$ | 60 |
| 22 | Silane A (15.1) | o-Toluidine (10.7) | Methanol (25.0) | R/3 | R*CH(SH)CH$_2$NHC$_6$H$_4$-2-CH$_3$ | 70 |
| 23 | Silane A (12.6) | 3-(n-Butylamino)-propyltrimethoxy-silane (23.5) | Hexane (30.0) | 50/36 | R*CH(SH)CH$_2$N(n-C$_4$H$_9$)(CH$_2$)$_3$—Si(OCH$_3$)$_3$ | 87 |

[1] R: Boiled under reflux, temperature range 50°–125° C.
[2] 0.1 parts benzylmercaptan added to inhibit polymerization
R*: (CH$_3$O)$_3$Si(CH$_2$)$_3$OCH$_2$—

EXAMPLES 24 to 44

A variety of silica-filled rubber compounds were prepared using the formulations of Table II and the same procedure. The silane coupling agents employed were the mercapto and amino substituted silane products of Examples 2 to 12, 14 to 17, 18, 19 and 21 to 23 above and are identified as Silanes A to T respectively in TABLE III below. Thus, said Silanes A to T have the structural formulas given for the products in above Examples 2 to 12, 14 to 17, 18, 19 and 21 to 23 respectively.

TABLE II

| Formulation | (Parts by Weight) |
|---|---|
| Styrene-Butadiene Rubber[1] | 100 |
| Silica Filler[2] | 35 |
| Silane Coupling Agent | Varied* |
| Softener Oil[3] | 8.0 |
| BBS[4] | 1.2 |
| DOTG[5] | 2.5 |
| Sulfur | 1.6 |
| Zinc Oxide | 4.0 |
| Stearic Acid | 1.0 |

[1] SBR 1502
[2] Precipitated silica (Hi-Sil 233, Trademark of PPG Industries, Inc.)
[3] Sundex 790, an aromatic processing oil (Trademark of Sun Oil Co.)
[4] N-t-butyl-2-benzothiazole sulfenamide
[5] Di-ortho-tolyl guanidine
*As shown in TABLE III below.

Each formulation was prepared using a 2 roll rubber mill having a roll temperature of about 130° F. The rubber polymer was charged to the rubber mill and milled until smooth and plastic. Then a small portion of the filler was added to the polymer band, followed by the addition of more filler along with the silane coupling agent which was added dropwise and concurrently with the filler. After all the silane and about half of the filler had been added the softening oil was added concurrently with the remainder of the filler. After an intimate milled mixture of the styrenebutadiene rubber, silica filler, silane coupling agent and softener was obtained, the sulfur, accelerators and other ancillary ingredients were added and the mixture further milled until an intimate dispersion was obtained. After storing at ambient room conditions for at least 16 hours, the mixture was remilled until plastic. Molded preformed sheets were cut from the remilled mixture of each formulation and then vulcanized in the same manner in a mold under pressure at 320° F. to 340° F. After resting at ambient room conditions for at least 16 hours the physical properties of the vulcanized molded rubber composites were then measured and the results recorded as shown in TABLE III.

TABLE III

| Ex. No. | Silane Coupling Agent (Parts by Wt.) | 300% Tensile Modulus (psi)[1] | Tensile Strength (psi)[1] | Elongation at Break (%)[1] | Tear Strength (psi)[2] |
|---|---|---|---|---|---|
| 24 | Control-No Silane | 353 | 3069 | 760 | 192 |
| 25 | Silane A (2.02) | 517 | 2610 | 650 | 253 |
| 26 | Silane B (1.28) | 560 | 3177 | 700 | 228 |
| 27 | Silane C (1.26) | 483 | 2819 | 677 | 251 |
| 28 | Silane D (1.40) | 614 | 2896 | 644 | 260 |
| 29 | Silane E (1.20) | 735 | 3084 | 600 | 289 |
| 30 | Silane F (1.25) | 740 | 2905 | 537 | 289 |
| 31 | Silane G (1.90) | 557 | 3676 | 727 | 264 |
| 32 | Silane H (1.40) | 739 | 3053 | 560 | 273 |
| 33 | Silane I (1.75) | 519 | 3069 | 690 | 282 |
| 34 | Silane J (1.60) | 780 | 3180 | 577 | 293 |
| 35 | Silane K (1.85) | 669 | 3363 | 654 | 280 |
| 36 | Silane L (3.2) | 659 | 2739 | 587 | 260 |
| 37 | Silane M (3.0) | 546 | 2824 | 640 | 250 |
| 38 | Silane N (1.60) | 480 | 2471 | 657 | 230 |
| 39 | Silane O (1.60) | 590 | 2630 | 623 | 250 |

TABLE III-continued

| Ex. No. | Silane Coupling Agent (Parts by Wt.) | 300% Tensile Modulus (psi)[1] | Tensile Strength (psi)[1] | Elongation at Break (%)[1] | Tear Strength (psi)[2] |
|---|---|---|---|---|---|
| 40 | Silane P (1.60) | 549 | 2505 | 600 | 240 |
| 41 | Silane Q (1.30) | 431 | 2929 | 707 | 244 |
| 42 | Silane R (1.90) | 700 | 2900 | 630 | 250 |
| 43 | Silane S (1.90) | 763 | 2822 | 550 | 283 |
| 44 | Silane T (1.04) | 550 | 2500 | 620 | 240 |

[1] Tested in compliance with ASTM D-412
[2] Tested in compliance with ASTM D-624

The above data demonstrates a significant improvement in the tensile modulus of the silane containing vulcanized rubber compound of Examples 25 to 44 over the non-silane containing vulcanized rubber compound of control Example 24.

EXAMPLE 45

About 1.0 grams of the 1-dimethylamino-2-mercapto-4-oxa-7-(trimethoxysilyl) heptane product of Example 3 above, along with about 5.0 grams of methanol and about 1.0 grams of glacial acetic acid was added to a 50 cc beaker. Water was then slowly added until the aqueous mixture became hazy. The mixture was then stirred until it cleared. Another increment of water was added until the mixture was hazy. The mixture was again stirred until it cleared. This procedure was repeated until about 20.0 grams of water had been added. Hydrolysis and condensation to a homopolymeric siloxane formulation having the siloxy unit $(CH_3)_2NCH_2CH(SH)CH_2O(CH_2)_3SiO_{1.5}$ was confirmed by infrared spectroscopy analysis. The siloxane concentrate product was found to be stable, i.e. no gel or precipitate formation, for more than 98 hours.

EXAMPLE 46

The procedure of Example 45 was repeated except that the 1-piperidino-2-mercapto-4-oxa-7-(trimethoxysilyl) heptane product of Example 4 above was employed as the silane starting material. Hydrolysis and condensation to a homopolymeric siloxane formulation having the siloxy unit.

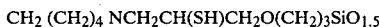

was confirmed by infrared spectroscopy analysis. The siloxane concentrate product was found to be stable, i.e. no gel or precipitate formation, for more than 98 hours.

EXAMPLE 47

The procedure of Example 45 was repeated except that the 1-anilino-2-mercapto-4-oxa-7-(trimethoxysilyl) heptane product of Example 6 above was employed as the silane starting material and 0.1 grams of concentrated HCl was employed in place of the glacial acetic acid. Hydrolysis and condensation to a homopolymeric siloxane formulation having the siloxy unit $C_6H_5NHCH_2CH(SH)CH_2O(CH_2)_3SiO_{1.5}$ was confirmed by infrared spectroscopy analysis. The siloxane concentrate product was found to be stable, i.e. no gel or precipitate formation, for 24 hours.

EXAMPLE 48

This example illustrates the production of a thermoset resin-glass fabric laminate article of manufacture.

An 0.1% by weight aqueous solution of 1-dimethylamino-2-mercapto-4-oxa-7-(trimethoxysilyl) heptane prepared from the concentrate product of Example 45 was used to treat twelve 7-inch wide woven glass fabric strips by dipping the glass trips into the solution. The treated woven glass fabric was then hung to dry at ambient temperature for 20 minutes and then dried in a forced air oven at 135° C. for about 2 to 3 minutes. The dried treated glass fabric was then cut into 12 inch squares and used to prepare a dry sandwich laminate by alternating twelve plies of treated glass fabric and eleven plies of a thermoset resin which was prepared by mixing 300.0 parts by weight of an epoxide resin and 45.0 parts by weight of meta-phenylene diamine. The laminate was then pressed to dimensioning stops in a preheated press for 30 minutes at 250° C. and post cured in a forced air oven at 200° C. for one hour.

The laminate was then cut into ten 4×½ inch test specimens and tested for flextural strength both initially and after immersion in boiling water after 72 hours, according to ASTM Specification D-790 using a Baldwin-Tate Tester.

The test specimens showed an initial flexural dry strength of 67,433 psi and a flexural wet strength of 62,491 after 72 hours in boiling water. In addition, the test specimens showed a percent wet retention (i.e. flexural wet strength, psi divided by flexural dry strength, psi times 100) of 92.6 and a % water pickup (i.e. wet weight of specimen minus dry weight of specimen divided by dry weight of specimen times 100) of 1.36. By comparison a glass laminate prepared in the same manner but from unfinished glass fabric had an initial flexural dry strength of 56,643, a flexural wet strength of 31,090, a % wet retention of 54.9 and a % water pick-up of 1.52.

EXAMPLE 49

The procedure of Example 48 was repeated except that an 0.1% by weight aqueous solution of 1-piperidino-2-mercapto-4-oxa-7-(trimethoxysilyl) heptane prepared from the concentrate product of Example 46 was employed as the silicon coupling agent.

The laminate test specimens so prepared showed an initial flexural dry strength of 76,980 psi and a flexural wet strength of 62,670 after 72 hours in boiling water. In addition, the test specimens showed a percent wet retention (i.e. flexural wet strength, psi divided by flexural dry strength, psi times 100) of 81.4 and a % water pick-up (i.e. wet weight of specimen minus dry weight of specimen divided by dry weight of specimen times 100) of 1.31.

EXAMPLE 50

The procedure of Example 48 was repeated except that an 0.1% by weight aqueous solution of 1-anilino-2-mercapto-4-oxa-7-(trimethoxysilyl) heptane prepared from the concentrate product of Example 47 was employed as the silicon coupling agent.

The laminate test specimens so prepared showed as initial flexural dry strength of 77,711 psi and a flexural wet strength of 63,433 after 72 hours in boiling water. In addition, the test specimens showed a percent wet retention (i.e. flexural wet strength, psi divided by flextural dry strength psi times 100) of 81.6 and a % water pick-up (i.e. wet weight of specimen minus dry weight of specimen divided by dry weight of specimen times 100) of 1.29.

EXAMPLE 51

This example illustrates the pretreatment of a silica filler with an amino substituted mercaptan silicon coupling agent.

One thousand parts by weight of a silica filler (Hi-Sil 233) was dried at 80° C. for 18 hours and cooled to room temperature. About 16.4 parts by weight of the 1-dimethylamino-2-mercapto-4-oxa-7-(trimethoxysilyl) heptane product of Example 3 above was mixed with about 150 parts by weight of a 90/10 (methanol/water) solvent and stirred for 20 minutes. The aqueous mixture was charged into a large dropping funnel attached to a twin shell blender. About 650 parts by weight of the dried silica filler was then added at a steady rate and the total blend mixed for 20 minutes. The wet silica treated mixture was then charged to a large pan and dried for 18 hours at 80° C. After drying the amino substituted mercapto silicon treated filler so obtained was weighed for use in elastomer formulation.

EXAMPLE 52

The procedure of Example 51 was repeated except that the 1-piperidino-2-mercapto-4-oxa-7-(trimethoxysilyl) heptane product of Example 4 above was employed as the silane starting material. After drying the amino substituted mercapto silicon treated filler so obtained was weighed for use in elastomer formulation.

EXAMPLE 53

The procedure of Example 51 was repeated except that the 1-anilino-2-mercapto-4-oxa-7-(trimethoxysilyl) heptane product of Example 6 above was employed as the silane starting material. After drying the amino substituted mercapto silicone treated filler so obtained was weighed for use in elastomer formulation.

EXAMPLES 54 TO 60

Seven vulcanized silica-filled rubber compounds were prepared using the formulations in TABLE IV and the same procedure. The silane coupling agents employed in Examples 55, 57 and 58 were the 1-dimethylamino-2-mercapto-4-oxa-7-(trimethoxysilyl) heptane product of Examples 3 above, the 1-piperidino-2-mercapto-4-oxa-7-(trimethoxysilyl)heptane product of Example 4 above and the 1-anilino-2-mercapto-4-oxa-7-trimethoxysilyl heptane product of Example 6 above, respectively. The filler and coupling agents employed in Examples 56, 58 and 60 were the amino substituted mercapto silicon pretreated silica filler product of Example 51 above, the amino substituted mercapto silicon pretreated silica filler product of Example 52 above, and the amino substituted mercapto silicon pretreated silica filler product of Example 53 above, respectively.

TABLE IV

| Formulation | Ex. 54 (Parts by Weight) | Ex. 55 (Parts by Weight) | Ex. 56 (Parts by Weight) | Ex. 57 (Parts by Weight) | Ex. 58 (Parts by Weight) | Ex. 59 (Parts by Weight) | Ex. 60 (Parts by Weight) |
|---|---|---|---|---|---|---|---|
| Styrene-Butadiene Rubber* | 100 | 100 | 100 | 100 | 100 | 100 | 100 |
| Silica Filler* | 35 | 35 | As Described[1] | 35 | As Described[2] | 35 | As Described[3] |
| Silicon Coupling Agent | None | 2.2 | | 2.6 | | 2.8 | |
| Softener Oil* | 8.0 | 8.0 | 8.0 | 8.0 | 8.0 | 8.0 | 8.0 |
| BBS* | 1.2 | 1.2 | 1.2 | 1.2 | 1.2 | 1.2 | 1.2 |
| DOTG* | 2.5 | 2.5 | 2.5 | 2.5 | 2.5 | 2.5 | 2.5 |
| Sulfur | 1.6 | 1.6 | 1.6 | 1.6 | 1.6 | 1.6 | 1.6 |
| Zinc Oxide | 4.0 | 4.0 | 4.0 | 4.0 | 4.0 | 4.0 | 4.0 |
| Stearic Acid | 1.0 | 1.0 | 1.0 | 1.0 | 1.0 | 1.0 | 1.0 |

*Same as Defined in TABLE I
[1] 37.2 Parts by weight of the amino substituted mercapto silicon pretreated silica filler product of Example 56
[2] 37.6 parts by weight of the amino substituted mercapto silicon pretreated silica filler product of Example 57
[3] 37.8 Parts by weight of the amino substituted mercapto silicon pretreated silica filler product of Example 58

Each formulation in TABLE IV above was prepared in the same manner as described in Examples 24 to 44, as were the vulcanized composites thereof. The physical properties of said vulcanized rubber products are given in TABLE V below.

TABLE V

| Properties of Rubber Compounds | Example 54 | Example 55 | Example 56 | Example 57 | Example 58 | Example 59 | Example 60 |
|---|---|---|---|---|---|---|---|
| 300% Tensile Modulus (psi)* | 234 | 481 | 500 | 467 | 398 | 667 | 975 |
| Tensile Strength (psi)* | 2906 | 3377 | 4093 | 4425 | 3736 | 3192 | 3831 |
| Elongation at Break (%)* | 840 | 755 | 763 | 803 | 798 | 679 | 770 |
| Tear Strength | | | | | | | |

TABLE V-continued

| Properties of Rubber Compounds | Example 54 | Example 55 | Example 56 | Example 57 | Example 58 | Example 59 | Example 60 |
|---|---|---|---|---|---|---|---|
| (psi)* | 153 | 248 | 238 | 245 | 236 | 307 | 250 |

*Same as defined in TABLE II.

The above data demonstrates a significant improvement in the tensile modulus of the silicon containing vulcanized rubber compounds, regardless of whether the silicon was employed as a neat silane (Examples 55, 57 and 59) or in the form of a silicon pretreated filler (Examples 56, 58 and 60) over the non-silicon containing vulcanized rubber compound of control Example 54.

EXAMPLE 61

About 10.0 grams of the 1-dimethylamino-2-mercapto-4-oxa-7-(trimethoxysilyl) heptane product of Example 3 above and about 0.92 grams of water and 3.0 grams of methanol were charged to a 100 ml flask and stirred until homogeneous. The flask was stoppered tightly and allowed to stand for two weeks. Hydrolysis and condensation of the silane monomer to a homopolymeric siloxane formulation having the siloxy unit,

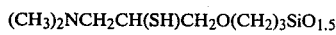
$(CH_3)_2NCH_2CH(SH)CH_2O(CH_2)_3SiO_{1.5}$ in the aqueous solution was followed and confirmed by infrared spectroscopy analysis.

EXAMPLE 62

The procedure in Example 61 was repeated except that the 1-piperidino-2-mercapto-4-oxa-7-(trimethoxysilyl) heptane product of Example 4 above along with 0.73 grams of water and 10.73 grams of methanol were employed. Hydrolysis and condensation of the silane monomer to a homopolymeric siloxane formulation having the siloxy unit

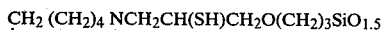
$\overline{CH_2 (CH_2)_4 NCH_2CH(SH)CH_2O(CH_2)_3SiO_{1.5}}$ in the aqueous solution was followed and confirmed by infrared spectroscopy analysis.

EXAMPLE 63

The procedure in Example 61 was repeated except that 1-anilino-2-mercapto-4-oxa-7-(trimethoxysilyl)heptane product of Example 6 above along with 0.65 grams of water and 10.65 grams of methanol were employed. Hydrolysis and condensation of the silane monomer to a homopolymeric siloxane formulation having the siloxy unit

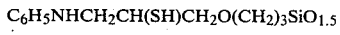
$C_6H_5NHCH_2CH(SH)CH_2O(CH_2)_3SiO_{1.5}$ in the aqueous solution was followed and confirmed by infrared spectroscopy analysis.

EXAMPLE 64

This example illustrates the production of a copolymeric mercapto and amino substituted siloxane.

About 10.0 grams of the 1-dimethylamino-2-mercapto-4-oxa-7-(trimethoxysilyl)heptane product of Example 3 above, about 4.6 grams of methyl trimethoxysilane, about 1.84 grams of water and about 3.0 grams of methanol were charged to a 100 ml. flask and stirred until homogeneous. The solution was allowed to stand for about two weeks at ambient temperatures. Hydrolysis and condensation of the two silane monomers to a copolymeric siloxane formulation having the siloxy units

$(CH_3)_2NCH_2CH(SH)CH_2O(CH_2)_3SiO_{1.5}$ and $CH_3SiO_{1.5}$ in the aqueous solution was followed and confirmed by infrared spectroscopy analysis.

EXAMPLE 65

The procedure of Example 64 was repeated except that the 1-piperidino-2-mercapto-4-oxa-7-(trimethoxysilyl)heptane product of Example 4 above, 3.73 grams of the methyl trimethoxysilane, 1.46 grams of water and 15.2 grams of methanol were employed. Hydrolysis and condensation of the two silane monomers to a copolymeric siloxane formulation having the siloxy units

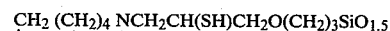
$\overline{CH_2 (CH_2)_4 NCH_2CH(SH)CH_2O(CH_2)_3SiO_{1.5}}$ and $CH_3SiO_{1.5}$ in the aqueous solution was confirmed by infrared spectroscopy analysis.

EXAMPLE 66

The procedure in Example 64 was repeated except that the 1-anilino-2-mercapto-4-oxa-7-(trimethoxysilyl)-heptane product of Example 6 above, 3.3 grams of the methyl trimethoxysilane, 1.3 grams of water and 14.6 grams of methanol were employed. Hydrolysis and condensation of the two silane monomers to a copolymeric siloxane formulation having the siloxy units

$C_6H_5NHCH_2CH(SH)CH_2O(CH_2)_3SiO_{1.5}$ and $CH_3SiO_{1.5}$ in the aqueous solution was confirmed by infrared spectroscopy analysis.

EXAMPLE 67

About 9.2 grams of aniline and 50 grams of methanol were charged to an aqueous homopolymeric siloxane hydrolyzate product having the siloxy unit

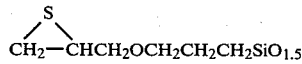

prepared as described in Example 21 of said concurrently filed U.S. application No. (D-9972). The mixture was then heated for four hours at reflux upon which time it was cooled and methanol removed under reduced pressure to obtain an aqueous solution of a homopolymeric siloxane hydrolyzate product having the siloxy unit

$C_6H_5NHCH_2CH(SH)CH_2O(CH_2)_3SiO_{1.5}$

The formation of said homopolymeric siloxane hydrolyzate was confirmed by infrared spectroscopy analysis.

The mercaptan titer by AgNO$_3$ titration of the hydrolyzate was 1.48 eq SH/Kg. product.

EXAMPLE 68

About 9.2 grams of aniline and 50 grams of methanol were charged to an aqueous copolymeric siloxane hydrolyzate product having the siloxy units

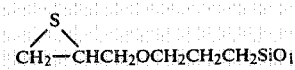

and CH$_3$SiO$_{1.5}$, prepared as described in Example 22 of said concurrently filed U.S. Application No. (D-9972). The mixture was then heated for four hours at reflux upon which time it was cooled and methanol removed under reduced pressure to obtain an aqueous solution of a copolymeric hydrolyzate product having the siloxy units C$_6$H$_5$NHCH$_2$CH(SH)CH$_2$O(CH$_2$)$_3$SiO$_{1.5}$ and CH$_3$SiO$_{1.5}$. The formation of said copolymeric siloxane hydrolyzate was confirmed by infrared spectroscopy analysis.

EXAMPLES 69 TO 77

A series of vulcanized silica-filled rubber compounds were prepared by repeating the same procedure of Examples 24 to 44 using the same formulation in TABLE II and the following silicon coupling agents. The silicon coupling agent of Example 70 was the amino substituted mercapto silane product of Example 3 above, and is identified as Silane C in TABLE VI. The silicon coupling agent of Example 71 was the homopolymeric amino substituted mercapto siloxane hydrolyzate solution product of Example 61 above and is identified as Siloxane AA in TABLE VI. The silicon coupling agent of Example 72 was the copolymeric amino substituted mercapto siloxane hydrolyzate solution product of Example 64 above, and is identified as Siloxane BB in TABLE VI. The silicon coupling agent of Example 73 was the amino substituted mercapto silane product of Example 6 above, and is identified as Silane E in TABLE VI. The silicon coupling agent of Example 74 was the homopolymeric amino substituted mercapto siloxane hydrolyzate solution product of Example 63 above, and is identified as Siloxane CC in TABLE VI. The silicone coupling agent of Example 74 was the copolymeric amino substituted mercapto siloxane hydrolyzate solution product of Example 66 above, and is identified as Siloxane DD in TABLE VI. The silicon coupling agent of Example 76 was the homopolymeric amino mercapto substituted siloxane hydrolyzate solution product of Example 67 above and is identified as Siloxane EE in TABLE VI. The silicone coupling agent of Example 77 was the copolymeric amino substituted mercapto siloxane hydrolyzate solution product of Example 68 above, and is identified as Siloxane FF in Table VI. The amount of silicon coupling agent employed is given TABLE VI as are the physical properties for the vulcanized molded rubber products so produced.

TABLE VI

| Ex. No. | Silicon Coupling Agent (Parts by Wt.) | 300% Tensile Modulus (psi)* | Tensile Strength (psi)* | Elongation at Break (%)* | Tear Strength (psi)* |
|---|---|---|---|---|---|
| 69 | Control, None | 234 | 2906 | 840 | 153 |
| 70 | Silane C (2.2) | 481 | 3377 | 755 | 248 |
| 71 | Siloxane AA (2.86) | 450 | 3266 | 745 | 218 |
| 72 | Siloxane BB (6.36) | 440 | 3264 | 762 | 223 |
| 73 | Silane E (2.8) | 667 | 3192 | 679 | 307 |
| 74 | Siloxane CC (5.47) | 576 | 3359 | 710 | 307 |
| 75 | Siloxane DD (7.45) | 655 | 3783 | 713 | 299 |
| 76 | Siloxane EE (3.68) | 694 | 3648 | 663 | 317 |
| 77 | Siloxane FF (4.73) | 690 | 2782 | 583 | 321 |

*Same as defined in TABLE II

The above data demonstrates a significant improvement in the tensile modulus of the silicon containing vulcanized rubber compounds of Examples 70 to 77 over the non-silicon containing vulcanized rubber compound of control Example 69.

EXAMPLE 78

This example illustrates a one-pot process for the preparation of 1-anilino-2-mercapto-4-oxa-7-(trimethoxysilyl)heptane.

About 23.6 grams of glycidoxypropyltrimethoxysilane, about 7.6 grams of thiourea and about 50 parts of methanol were charged to a 200 ml neck distillation flask equipped with a magnetic stirrer, thermometer well, water condenser and nitrogen gas by-pass. The mixture was then cooled and 18.6 grams of aniline was added and heated to reflux for three hours. The mixture was then cooled and the methanol was vacuum-stripped off. About 200 grams of n-hexane was then added and the product filtered. The n-hexane was then stripped off yielding about 32.0 grams of a silane product having the formula (CH$_3$O)$_3$Si(CH$_2$)$_3$OCH$_2$CH(SH)CH$_2$NHC$_6$H$_5$ The product was confirmed by infrared spectroscopy analysis and was also characterized by silver nitrate titration for the mercapto group i.e. the mercaptan titer by AgNO$_3$ titration was 2.19 eq. SH/Kg product.

A vulcanized silica-filled rubber product was prepared by repeating the same procedure in Examples 24 to 44 using the same formulation in TABLE II with about 3.2 parts by weight of the amino substituted mercapto silane product so prepared by the one-pot process above.

The physical properties of the vulcanized rubber product so produced are given in TABLE VII below.

TABLE VII

| 300% Tensile Modulus (psi)* | Tensile Strength (psi)* | Elongation at Break (%)* | Tear Strength (psi)* |
|---|---|---|---|
| 786 | 3188 | 593 | 308 |

*Same as defined in TABLE II.

As noted above, the amino substituted mercapto silicon compositions of matter are extremely effective coupling agents and thus offer exceptional promise in the production of filled-vulcanized rubber articles such as tires, gaskets, hoses, and other conventional mechanical rubber goods.

Various modifications and variations of this invention will be obvious to a worker skilled in the art and it is to be understood that such modifications and variations are to be included within the purview of this application and the spirit and scope of the appended claims.

What is claimed is:

1. An inorganic substrate treated with an organosilicon coupling agent selected from the class consisting of (i) amino substituted mercapto organosilanes having the formula

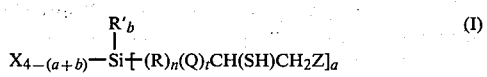

wherein R' is a monovalent hydrocarbon radical selected from the class consisting of hydrogen, hydrocarbon radicals and substituted hydrocarbon radicals.

wherein X is a hydrolyzable radical selected from the class consisting of alkoxy, aryloxy, acyloxy, secondary amino and aminooxy radicals;

wherein R is a divalent bridging group selected from the class consisting of hydrocarbon radicals, groups of the formula —R"OR"— and groups of the formula —R"SR"—, wherein R" is a divalent hydrocarbon radical;

wherein Q is an oxygen atom or a sulfur atom;

wherein Z is a monovalent organic amino radical, the nitrogen atom of which is directly bonded to the carbon atom of the (CH$_2$) group of the above formula;

wherein n has a value of 0 or 1, and t has a value of 0 or 1, with the proviso that when n is 0, then t is 0;

wherein a has a value of 1 to 3 and b has a value of 0 to 2, with the proviso that the sum of (a+b) is not greater than 3; (ii) amino substituted mercapto organosiloxane homopolymers consisting essentially of siloxy units having the formula

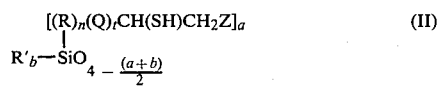

wherein R', R, Q, Z, n, t, a and b are the same as defined above; and (iii) amino substituted mercapto organosiloxane copolymers consisting essentially of at least one siloxy unit represented by formula (II) above and at least one siloxy unit represented by the formula

wherein R' is the same as defined in formula (II) above and wherein c has a value from 0 to 3 inclusive.

2. An inorganic substrate as defined in claim 1, wherein the substrate is a siliceous reinforcing material.

3. An inorganic substrate as defined in claim 2, wherein the organosilicon coupling agent is an amino substituted mercapto organosilane having the formula

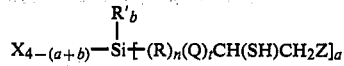

4. An inorganic substrate as defined in claim 3, wherein R' is an alkyl radical, wherein X is an alkoxy radical, wherein R is an alkylene or alkyleneoxyalkylene radical, and wherein n is 1, t is 0 and a is 1.

5. An inorganic substrate as defined in claim 4, wherein b is 0 and Z is an organic amino radical of the formula

wherein Z$^1$ and Z$^2$ are taken individually and Z$^1$ is an organic radical selected from the class consisting of alkyl, aryl, aralkyl, alkaryl and haloaryl radicals; hydroxy substituted alkyl, aryl, aralkyl and alkaryl radicals; alkoxy substituted alkyl, aryl, aralkyl and alkaryl radicals; mercapto substituted alkyl, aryl, aralkyl and alkaryl radicals; amino substituted alkyl, aryl, aralkyl and alkaryl radicals; and hydrolyzable silyl substituted alkyl, aryl, aralkyl and alkaryl radicals; and wherein Z$^2$ is hydrogen or a Z$^1$ radical as defined above.

6. An inorganic substrate as defined in claim 5, wherein X is methoxy or ethoxy, R is a propyleneoxymethylene radical, Z$^1$ is alkyl or aralkyl and Z$^2$ is hydrogen.

7. An inorganic substrate as defined in claim 6, wherein Z$^1$ is a p-toluidinyl radical.

8. An inorganic substrate as defined in claim 2, wherein the organosilicon coupling agent is an amino substituted mercapto organosiloxane homopolymer consisting essentially of siloxy units of the formula

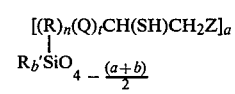

9. An inorganic substrate as defined in claim 8, wherein R' is an alkyl radical, wherein R is an alkylene or alkyleneoxyalkylene radical and wherein n is 1 and t is 0.

10. An inorganic substrate as defined in claim 9, wherein R is a propyleneoxymethylene radical and Z is an organic amino radical of the formula

wherein Z$^1$ and Z$^2$ are taken individually and Z$^1$ is an organic radical selected from the class consisting of alkyl, aryl, aralkyl, alkaryl, and haloaryl radicals; hydroxy substituted alkyl, aryl, aralkyl and alkaryl radicals; alkoxy substituted alkyl, aryl, aralkyl and alkaryl radicals; mercapto substituted alkyl, aryl, aralkyl and alkaryl radicals; amino substituted alkyl, aryl, aralkyl and alkaryl radicals; and hydrolyzable silyl substituted alkyl aryl, aralkyl and alkaryl radicals; and wherein Z$^2$ is hydrogen or a Z$^1$ radical as defined above.

11. An inorganic substrate as defined in claim 10, wherein $Z^1$ is an alkyl or aralkyl radical and $Z^2$ is hydrogen.

12. An inorganic substrate as defined in claim 11, wherein $Z^1$ is a p-toluidinyl radical.

13. An inorganic substrate as defined in claim 2, wherein the organosilicon coupling agent is an amino substituted mercapto organosiloxane copolymer consisting essentially of at least one siloxy unit of the formula

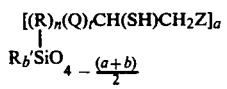

and at least one siloxy unit of the formula

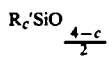

14. An inorganic substrate as defined in claim 13, wherein R' is a monovalent hydrocarbon radical, wherein R is an alkylene or alkyleneoxyalkylene radical, and wherein n is 1, t is 0 and a is 1.

15. An inorganic substrate as defined in claim 14, wherein R' is an alkyl radical.

16. An inorganic substrate as defined in claim 15, wherein R is a propyleneoxymethylene radical and wherein Z is an organic amino radical of the formula $$-NZ^1Z^2$$

wherein $Z^1$ and $Z^2$ are taken individually and $Z^1$ is an organic radical selected from the class consisting of alkyl, aryl, aralkyl, alkaryl and haloaryl radicals; hydroxy substituted alkyl, aryl, aralkyl and alkaryl radicals, alkoxy substituted alkyl, aryl, aralkyl and alkaryl radicals; mercapto substituted alkyl, aryl, aralkyl and alkaryl radicals; amino substituted alkyl, aryl, aralkyl and alkaryl radicals; and hydrolyzable silyl substituted alkyl, aryl, aralkyl and alkaryl radicals; and wherein $Z^2$ is hydrogen or a $Z^1$ radical as defined above.

17. An inorganic substrate as defined in claim 16, wherein $Z^2$ is hydrogen and $Z^1$ is an alkyl or aralkyl radical.

18. An inorganic substrate as defined in claim 17, wherein $Z^1$ is a p-toluidinyl radical.

19. An inorganic substrate as defined in claim 2, wherein the siliceous reinforcing material is selected from the class consisting of silica fillers, metal silicate fillers and glass fibers.

20. An inorganic substrate as defined in claim 2, wherein the amino substituted mercapto organosilicon coupling agent is employed in the form of a solubilized solution.

21. An inorganic substrate as defined in claim 2, wherein the amino substituted mercapto organosilicon coupling agent is employed in the form of an aqueous composition.

* * * * *

UNITED STATES PATENT AND TRADEMARK OFFICE
CERTIFICATE OF CORRECTION

PATENT NO. : 4,218,513
DATED : August 19, 1980
INVENTOR(S) : Williams et al

It is certified that error appears in the above—identified patent and that said Letters Patent is hereby corrected as shown below:

In column 22, in Table III's right hand-most column, last (i.e. lowest) entry, for "240" read --250--.

Signed and Sealed this

Twenty-third Day of June 1981

[SEAL]

Attest:

RENE D. TEGTMEYER

Attesting Officer     Acting Commissioner of Patents and Trademarks